US007718950B2

(12) United States Patent  
Saraf

(10) Patent No.: US 7,718,950 B2  
(45) Date of Patent: May 18, 2010

(54) HIGH RESOLUTION THIN FILM TACTILE DEVICE TO DETECT DISTRIBUTION OF STIMULI ON BY TOUCH

(76) Inventor: Ravi F. Saraf, 2649, Wilderness Ridge Cir., Lincoln, NE (US) 68512

( * ) Notice: Subject to any disclaimer, the term of this patent is extended or adjusted under 35 U.S.C. 154(b) by 180 days.

(21) Appl. No.: 11/810,113

(22) Filed: Jun. 4, 2007

(65) Prior Publication Data  
US 2008/0123078 A1 May 29, 2008

Related U.S. Application Data

(60) Provisional application No. 60/811,412, filed on Jun. 7, 2006.

(51) Int. Cl.  
*H01J 40/14* (2006.01)

(52) U.S. Cl. ............... 250/221; 250/216; 977/932

(58) Field of Classification Search .......... 250/221, 250/216, 214.1; 356/32, 614; 977/952–953, 977/932; 438/14  
See application file for complete search history.

(56) References Cited

U.S. PATENT DOCUMENTS

2006/0274049 A1* 12/2006 Spath et al. ............... 345/173  
2008/0093608 A1* 4/2008 Chik et al. ............... 257/89

* cited by examiner

*Primary Examiner*—Kevin Pyo  
(74) *Attorney, Agent, or Firm*—William L. Botjer

(57) ABSTRACT

A sensor to detect and map various mechanical stimuli spatially distributed over the area of contact with the surface of the sensor. The sensor is a thin film including a stack of alternating layers of nanoparticles and dielectric materials sandwiched between electrodes. By applying a bias between the electrodes, the applied stimuli to the sensor is converted to light and/or device-current through the stack. The optical signal may be directly focused on a photo detector, such as a digital camera, to image the distribution of the stimuli. The electronic signal in the form of spatial distribution of device-current over the area of contact may be obtained by patterning top and bottom electrodes and analyzed using standard electronics. The sensor has applications in many fields, including medicine, forensics, basic and applied research, and robotics.

17 Claims, 5 Drawing Sheets

HIGH RESOLUTION THIN FILM TACTILE DEVICE TO DETECT DISTRIBUTION OF STIMULI ON BY TOUCH

REFERENCE TO RELATED APPLICATIONS

This application claims priority of U.S. Provisional Application Ser. No. 60/811,412 filed on Jun. 7, 2006 by Ravi F. Saraf entitled "High Resolution Thin Film Device As Electronic Skin" the disclosure of which is hereby incorporated by reference.

STATEMENT OF GOVERNMENT INTEREST

This invention was made partially with U.S. Government support from the United States Office of Naval Research under grant number N00014-01-1-0977 and the National Science Foundation under grant number 0534812.

BACKGROUND OF THE INVENTION

1. Field of the Invention

The present invention relates to sensors to detect and map various stimuli spatially distributed over the area of contact with the surface of the sensor. More specifically, the present invention relates to a family of opto-electronic and electronic sensors that by touch or on physical contact with the surface of a body detects features, such as texture and roughness of the body's surface, variation in hardness of a body, palpable structure, shape of a solid object, static-charge on the surface of a body, and temperature distribution of a solid surface. This invention is a family of devices in a form of a thin-film that utilizes nanoparticles and polymers to convert the stimuli on touch over the area of contact to an electrical, or optical, or a combination of electrical and optical signals that can be processed using standard electronics to detect the distribution of the magnitude of the stimuli received over the area of contact. The abovementioned device can substitute for or act in conjunction with one or more human senses.

2. Description of Related Art

Broadly, the sensation of touch is the determination of distribution of physical properties such as, texture, roughness, hardness, static-charge, and temperature over the area of physical contact. The primary function of sense of touch is the determination of the magnitude of stress or pressure distribution over the area of physical contact between the sensor and the object surfaces to "feel" the texture, roughness, hardness and palpable features imbedded in the object tactile or touch sensors of substantial active area of contact is a critical component to advance noninvasive surgical procedures by giving a surgeon the "touch sensation", for example to determine various normal and diseased tissues of a patient. More specifically, tactile devices are used as medical devices to image the palpable structure in a breast to determine cancerous mass or tumor. It is also a critical component in the development of humanoid robots that can sense shapes, textures, hardness, and manipulate complex objects, which are not possible by vision alone. Touch (or tactile) sensors are usually made as a micro-electromechanical system composed of micro-machined deformable components or by integrating strain sensitive materials, such as magneto-resistive ceramics, piezoelectric polymers, and strain sensitive conducting elastomers. Tactile sensors based on change in the capacitance between two electrodes spaced by a polymer have also been designed using an array of such capacitors. Tactile sensors from optical data have been demonstrated where the contact stress distribution is calculated from the change in shape of the deformable sensor surface obtained by a camera. For small area devices, such as an array of capacitance sensors on an 8 by 8 matrix, a spatial resolution of 100 micrometers ($\mu m$) has been demonstrated. However, for a large area device of active (i.e., sensing) area of about 1 $cm^2$ or larger, the spatial resolution for stress distribution is at best in the approximately 2 mm range, which compares poorly with the approximately 40 $\mu m$ resolution achieved by the human finger.

Thus, there exists a need in the art for improved sensors to replace, complement, or augment one or more human senses of touch. Included among these are touch sensors to sense texture, imbedded palpable features, static charge and spatial variation of temperature. These devices find use in many fields, including the medical field, the sports and health fields, and robotics.

SUMMARY OF THE INVENTION

Touch or tactile sensors are gaining renewed interest as the level of sophistication in application of minimally invasive surgery and humanoid robots increases. However, the spatial resolution of current large-area tactile sensor of sensing area greater than 1 $cm^2$ lags by over an order of magnitude compared to the human finger. To address this shortcoming, the present invention provides an opto-electronic and an electronic tactile device, which can replace, complement, or augment the human sense of touch, and can be used in numerous other applications. The device is based, at least in part, on electronic tunneling using nanoparticles to form a sensor, which is coupled to computer equipment for analyzing and displaying information collected by the sensor. The exponential dependence between the current and the distance between the nanoparticles contributes to high sensitivity of the sensor. The cluster of the nanoparticles electrically percolating and connecting the top and bottom electrodes have a small lateral size leading to high spatial resolution of the tactile sensing.

To facilitate the description, the polarity (i.e. orientation) of the thin-film device is arbitrarily chosen as the top surface of the device where the physical contact is made to receive the stimuli. The bottom surface of the device may simply be a supporting substrate. The supporting substrate for an opto-electronic sensor is also transparent through which the optical signal is extracted. Furthermore, the fabrication is arbitrarily initiated from bottom side of the device.

As a general matter, the device of the invention comprises an insulating bottom substrate with an electrode upon which layers of nanoparticles and dielectric barriers are disposed. The electrode may be a continuous film or a film patterned into lines and other geometric shapes, such as squares and circles. The bottom electrode may be a conducting or semi-conducting material. The substrate may be comprised of any suitable material that is insulating, including, but not limited to, glasses, ceramics, or plastics. Upon the bottom electrode is disposed alternating layers of nanoparticles and dielectric barriers. The sequence may initiate with nanoparticles or the dielectric barrier layer, preferably the dielectric layer. Although the number of layers of nanoparticles and dielectric is not limited, as a general matter fewer than 10 and more than 4 of each layer is preferable. For example, upon the substrate could be a layer of dielectric barrier, an array of nanoparticles, a second layer of dielectric barrier, a second array of nanoparticles, a third layer of dielectric barrier, a third array of nanoparticles, and a fourth layer of dielectric barrier. Finally, the top surface of the device is also in contact with an electrode. A top electrode is included in the sensor to provide the second terminal to complete the electric circuit with the bottom electrode.

While not limited in size, shape, or material of fabrication, the top layer of the device including the electrode will depend on the nature of the stimuli for sensing. For sensing stimuli due to distribution of stress or pressure on the area of contact by features including, but not limited to, texture, palpable structure, hardness inhomogeneity, the top electrode will typically be supported on a film of flexible material, or a free-standing flexible film, or a flexible thin-film deposited on the multilayer device. The top electrode for sensing stress or pressure is a conducting or semi-conducting material. To sense stimuli such as temperature, the top electrode may be supported on a rigid to flexible substrate, or a rigid to flexible free-standing film, or the electrode is directly deposited on the multilayer device. The bottom electrode to sense temperature is a rigid to flexible. To sense stimuli such as charge, the top electrode is a flexible to rigid film made of poorly conducting, or ion-conducting, or semi-conducting materials.

According to the invention, the nanoparticles may be made of conducting, semi-conducting, or combinations thereof. Those of ordinary skill in the art appreciate that the size distribution of a batch of nanoparticles is gauged by the average size of the particle and the polydispersity index that is defined as the ratio of second moment average size divided by the average size. Those of ordinary skill in the art will further appreciate that larger the polydispesity index broader is the distribution. The average size or diameter of the nanoparticles is less than 100 nm, preferably less than 15 nm. The polydispersity index for the batch of nanoparticles used to fabricate the device is less than 10, preferable less than 2. Each layer of nanoparticles may be comprised of a single type of nanoparticle, or may have multiple different types of nanoparticles mixed together. It is preferred that each layer comprise the same chemical composition nanoparticle with a narrow size distribution of polydispersity index less than 2 and average diameter of less than 15 nm. While it is preferred that the nanoparticles be provided in monolayers, the invention encompasses use of thicker layers of nanoparticles in one or more than one of the layers of the sensor. Typically, the nanoparticles will self-assemble into a suitable array that functions within the present invention. In the lateral direction each layer of nanoparticles is conducting in a range at most up to 1 μm, preferably less than 100 nm.

The sensor of the invention comprises dielectric barriers between each layer of nanoparticles. The dielectric barrier(s) may comprise of any substance that is insulating and/or a weak ionic conductor that has conductivity less than $10^{-9}$ $\Omega^{-1}$-$cm^{-1}$. Examples of dielectric barrier materials include, but not limited to, combinations of a positively and negatively charged polyelectrolytes. The thickness of the dielectric barrier film is typically less than 25 nm, and preferably less than 10 nm thick.

To operate the device, a bias is applied between the electrodes. The bias is typically less than 100 V, preferably less than 30V. The bias causes a small current through the device. Application of stress or pressure on the top surface of the device produces a strain in the multilayer device that causes the particles to move closer by a small distance, for example less than 5 nm, such as 0.5 nm. The reversible strain causes a change in current through the device. The current increases monotonically as the magnitude of the local compressive strain increases. If the device contains a layer of nanoparticles made from a direct band-gap semiconductor, such as ZnS, CdS, and so on, there is a concomitant emission of electroluminescent light. The intensity of light, similar to the current, also increases monotonically as the magnitude of local compressive strain increases. Because the top surface of the device is flexible, the distribution of applied stress or pressure causes a corresponding distribution of strain in the film.

For opto-electronic devices, the bottom substrate and the electrode are transparent to allow collection and focusing of the electroluminescent light on an optical detector. An optical detector may be, but not limited to, a digital camera, array of photo diodes, or an array of photomultiplier detectors. Because the intensity of the emitted light corresponds to the magnitude of local stress, the focused image on the digital camera is a "stress image" of the stress or pressure distribution. For an electronic tactile device, the current distribution over the area of contact is obtained by patterning the top and bottom electrodes. For example, the top and bottom electrodes may be a parallel set-of-lines that are mutually perpendicular. For the electronic device, where only current distribution is measured, the nanoparticles do not have to be made from electroluminescent material. Those of ordinary skill in the art will appreciate that an opto-electronic tactile device can operate also as an electronic device by patterning the transparent bottom electrode and the top electrode similar to the patterned electrodes of the electronic tactile device. To measure stimuli from charge, the tactile device will be similar to the opto-electronic and electronic device to measure stress and pressure distribution, except the to substrate is not needed and the electrode will be a semi-conducting or weakly conducting film. To measure stimuli from temperature, the tactile device will be similar to the opto-electronic and electronic device to measure stress and pressure distribution, except the top layer including the electrode does not have to be flexible.

The image from the electroluminescent light on the optical detector and the current density from the parallel set-of-lines of the tactile devices may be connected to electronic hardware to supply power to the device, acquire data for data analysis, storage and display using standard equipment such as, but not limited to, computers, signal analyzers, and signal generators. The display will preferably be an image of the stimuli distribution where the grey scale represents the magnitude of the stimuli. Preferably, the response of the device is linear, such that the magnitude of the stimuli is linearly proportional to the electroluminescent intensity and/or current density so that the image displays the distribution quantitatively. Those of ordinary skill in the art will appreciate that a set of signal from the data acquisition and computation system can feed back to an electromechanical entity that holds the device and/or the power supply of the device to invoke a desired action.

In view of the above disclosure, this invention provides a system comprising at least one sensor device, at least one signal processing system, a computer, one power supply, and at least one connector connecting the sensor device to the processor. Generally speaking, this invention thus provides a system comprising at least one sensing means for sensing at least one stimulus; at least one processing means for receiving information regarding at least one stimulus and processing the information; and at least one connecting means for connecting the sensing means to the processing means.

BRIEF DESCRIPTION OF THE DRAWINGS

The accompanying drawings, which are incorporated in and constitute a part of this specification, illustrate one embodiments of the invention and together with the written description, serve to explain certain principles and features of the invention.

FIG. 1 illustrate a typical design of the device to demonstrate the working principle and function of the two families of device elements. The stimuli may be stress or pressure, or temperature, or charge.

FIG. 2 is a typical configuration of the device to measure distribution of stimuli over the area of contact for the opto-electronic and electronic tactile device.

DETAILED DESCRIPTION OF PREFERRED EMBODIMENTS OF THE INVENTION

Figure 1A:
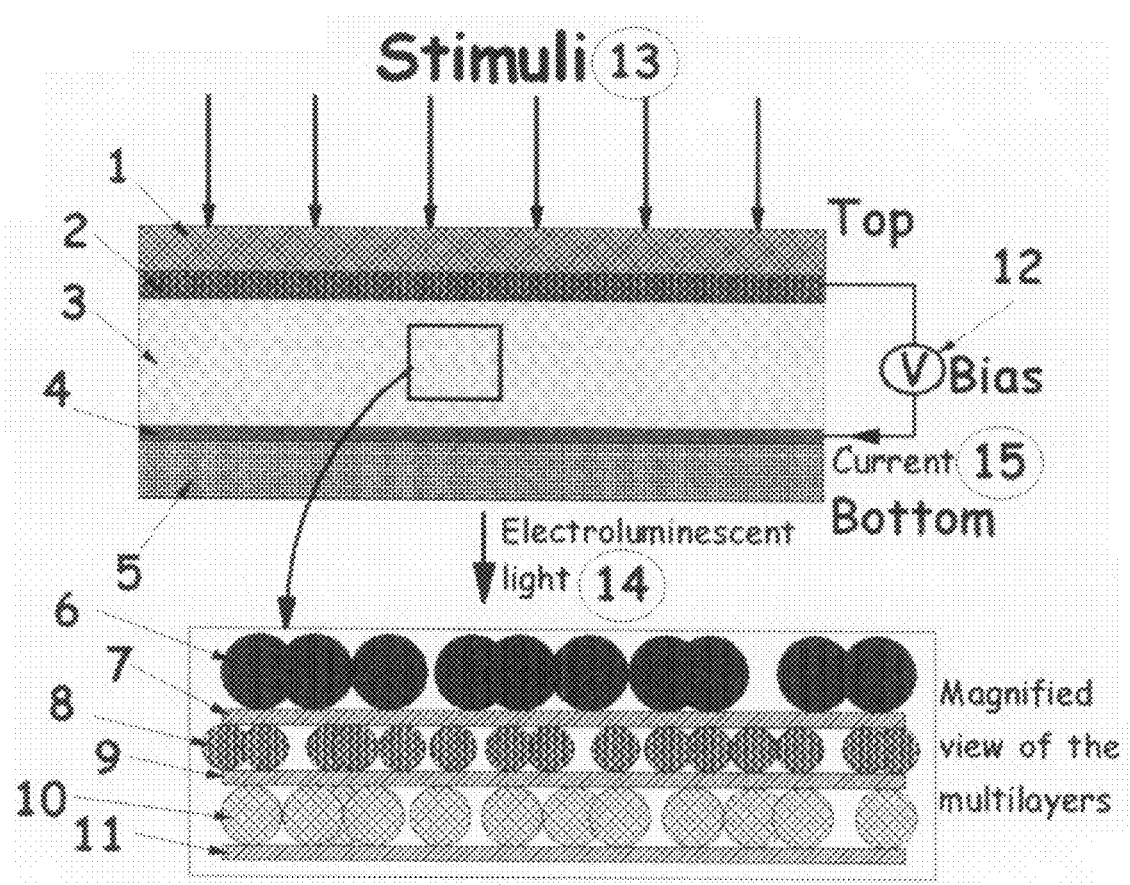
FIG. 1(a) is a cross-section of an Opto-electronic Device Element showing the typical components, and a magnified view of the multilayer device with stacked layers of dielectric and nanoparticles.

Reference will now be made in detail to various exemplary embodiments of this invention, examples of which are illustrated in the accompanying drawings. The following detailed description should not be understood as a limitation on the scope of this invention, but should rather be considered as it is intended —to provide details on certain features and aspects of the invention. This invention is two families of devices to measure the stimuli over the area of contact. In the first family of devices, referred to as opto-electronic device, the stimuli is converted to an optical and electrical signal. In the second family of devices, referred to as electronic device, the stimuli is converted to an electrical signal.

To facilitate the description, the polarity (orientation) of the thin-film devices (FIG. 1 and FIG. 2) is arbitrarily chosen as the top surface of the device where the physical contact is made to receive the stimuli. The bottom surface of the device is simply a supporting substrate and, in certain designs the surface through which the optical signal is extracted. Those of ordinary skill in the art will appreciate that the fabrication of the device may be initiated from the top or bottom surface, and the top surface that receives the stimuli on contact could be the bottom surface of the device. In overview, the Opto-electronic device of FIG. 1a and the Electronic Device of FIG. 1b comprise a flexible, insulating top layer (1,16); a top electrode (2,17); a "sandwich' of active layers (3,18); a bottom electrode (4,19) and a substrate (5,20)

Figure 1B:
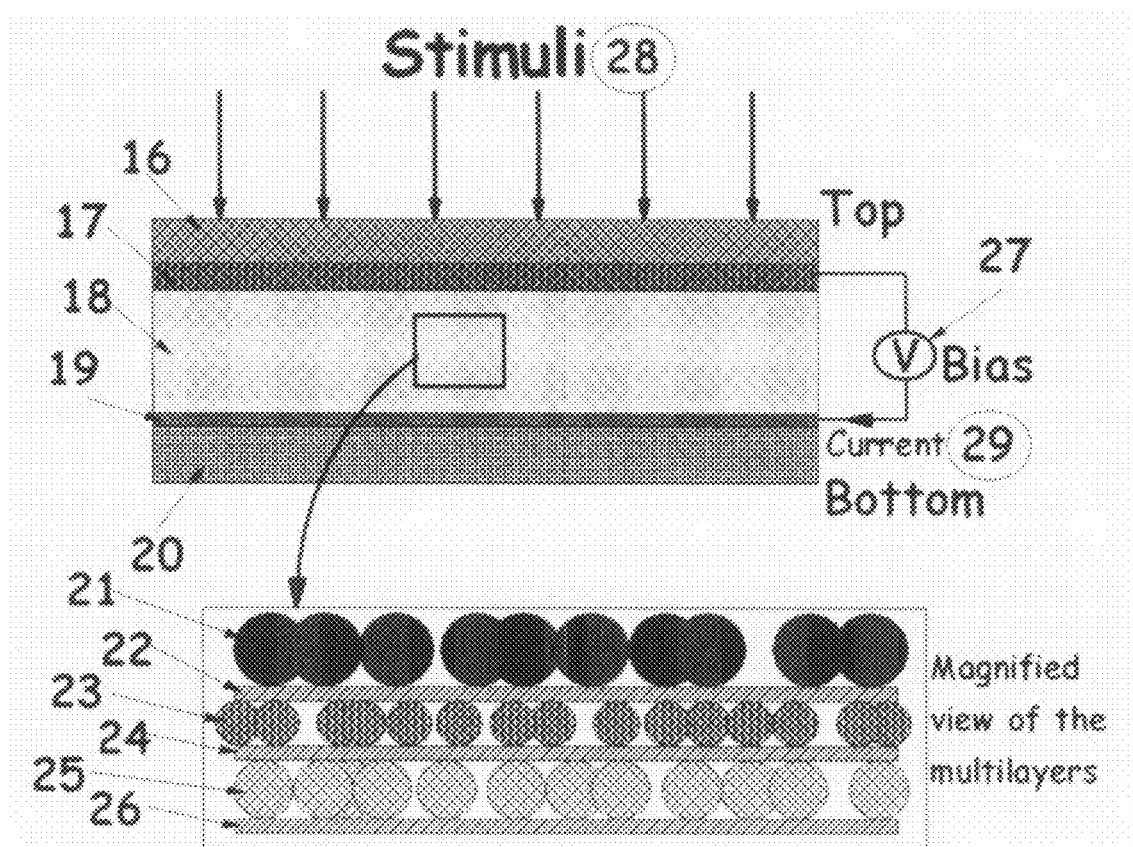
FIG. 1(b) is a cross-section of an Electronic Device Element showing the typical components, and a magnified view of the multilayer device with stacked layers of dielectric and nanoparticles. In this device element, the layers of nanoparticles do not have to have electroluminescent nanoparticles.

To describe the function of the two families of devices, the basic sensing unit to detect the average stimuli at small elemental area that is a small fraction of the total area of contact is considered. The "device element" is shown in FIGS. 1a and 1b for the two families of devices. The active layers (3,18); comprises layers of nanoparticles (6,8,10 & 21,23,25) spaced by dielectric layers (7,9,11 & 22,24,26) which are sandwiched between two electrodes (2,4 & 17,19). The electrodes are of conducting or semi-conducting material. The nanoparticle layers (6,8,10 & 21,23,25) in the lateral direction is conducting over a range below 10 µm, and preferably below 100 nm. The range of conduction is defined as the length over which the particles in the layer are close enough for the charge to conduct or percolate. The dielectric layer is thin enough so the multilayer structure is conducting along the thickness direction. The dielectric layer is less than 25 nm thick, preferably less than 10 nm.

The device is a stack of at least one type of nanoparticle layer, preferably at least 5 layers of nanoparticles spaced by layers of dielectric material. In the first family of devices, the electro-optical device (FIG. 1(a)), at least one layer of nanoparticles is made of material that exhibits electroluminescence (for example, 8), and consistent with the arbitrary convention stated in the prior paragraph. The bottom electrode (4) is made of a transparent conductor or semi-conductor. In the second family of devices, the electronic device (FIG. 1(b)), the nanoparticles (for example in layers 21, 23, 25) are made of materials that need not be electroluminescent and no specific restriction applies for the optical property of the electrodes (17,19). For both type of devices, for operation, a potential difference V (12 & 27) is applied between the two electrodes. Typically, the applied potential between the electrodes is below 100 V, preferably below 30 V. The response of the device to stress or pressure applied on the flexible, insulating top layer (1 & 16) will depend on the type of the device. For the electro-optical device FIG. 1a, both the current (15) between the electrodes and the intensity of the electroluminescent light (14) will change as a function of the applied stress or pressure (13). For the electronic device FIG. 1b, only the current between the electrodes (29) will change as a function of the applied stress or pressure (28). Typically, for both type of devices the current will increase as the magnitude of compressive stress or pressure increases. For the electro-optical device (FIG. 1(a)), typically, the intensity of the electroluminescent light will also increase as the magnitude of applied stress or pressure increases.

According to this invention, the nanoparticles (6,8,10 & 21,23,25) in the layers may be made of conducting, semi-conducting, or combinations thereof. Numerous nanoparticles comprising various different substances having conducting and semi-conducting properties are known in the art. Examples of conducting nanoparticles include, but not limited to, gold, silver, copper with phosphorus impurity, and mixtures of metals. Examples of semi-conducting nanoparticles include, but not limited to, CdS, CdSe, ZnS, GaAs, BN, GaP, and doped compounds such as ZnS doped with $Mn^{+2}$. Examples of composite conducting and semi-conducting nanoparticles include, but not limited to, Au coated CdS, Au coated $SiO_2$, Au coated $TiO_2$, Au coated Co, FePt coated $Fe_3O_4$, and Au coated Ag, and $Cd_xZn_{1-x}S$ where x is less than 1. The size distribution of a batch of nanoparticles is gauged by the polydispersity index that is defined as the ratio of second moment average size divided by the first moment average size. The first moment average size is simply the average size of the nanoparticles in the batch. The average size or diameter of the nanoparticles is less than 100 nm, preferably less than 15 nm. The polydispersity index for the batch of nanoparticles used to fabricate the device is less than 10, preferable less than 2. Methods of synthesizing nanoparticles are known in the art and need not be detailed herein.

Each layer of nanoparticles may be comprised of a single type of nanoparticle or may have multiple different types of nanoparticles mixed together. Likewise, the nanoparticles of any one layer may be all from the same batch of nanoparticles, or same material from different batches with different or similar average size and polydispersity. Furthermore, nanoparticles of differing layers may be of similar or different material, and similar or different average size and size distribution. Although any permutation of size and material may be included in a single layer and between different layers, it is preferred that each layer be comprised of nanoparticles of the same chemical composition with a size distribution of polydispersity index less than 2 and average diameter of less than 15 nm. While it is preferred that the nanoparticles be provided in monolayers, the invention encompasses use of thicker layers of nanoparticles in one or more of the layers of the sensor.

The identity of the material and size of the nanoparticles is not critical to practice of the invention. Rather, any combination of metal and/or semiconducting nanoparticle of any average size and distribution may be used. Likewise, arrangement of the nanoparticles in each layer with respect to each other need not be monitored or adjusted during fabrication of the sensor. Typically, the nanoparticles will self-assemble into a suitable array that functions within the present invention. The conductivity in the lateral direction in each layer of nanoparticle may range at most up to 1 µm, preferably less than 100 nm.

The sensor of the invention comprises dielectric barriers (7,9,11 & 22,24,26) between each layer of nanoparticles (magnified schematic in FIG. 1). The dielectric barrier(s) may comprise of any substance that is insulating and/or a weak ionic conductor that has conductivity less than $10^{-9}$ $\Omega^{-1}\text{-cm}^{-1}$. Examples of dielectric barrier materials include, but not limited to, combinations of a positively and negatively charged polyelectrolyte, such as poly(lysine) and DNA (deoxyribo nucleic acid), or poly(styrene sulfonate) and poly (allylamine hydrochloride). The barrier dielectric film may be of any lateral size, conforming to the arbitrarily shaped substrate. The thickness of the dielectric barrier film is typically less than 25 nm thick, and is preferably less than 10 nm thick, such as about 5 nm or less thick. Methods of synthesizing polymers and other dielectric films are known in the art and need not be detailed herein.

The bottom electrode (4 & 19) may be a conducting or semiconducting element, alloy or a compound on a substrate (5 & 20). Examples of the bottom electrode include, but not limited to, gold, Si, indium-tin-oxide (ITO), gold-tin alloy, poly(aniline), poly(thiophene), and composites of carbon nanotube in polymer matrix. For electro-optical devices (FIG. 1(a)), the electrode (4) needs to be transparent or translucent for the electroluminescent light (14) to transmit. An example of a transparent electrode is indium tin oxide (ITO). For electronic devices (FIG. 1(b)) there is no special restriction on the optical property for the material used for the bottom electrode (19).

The bottom substrate (5 & 20) may be comprised of any suitable material that is insulating, including, but not limited to, glasses, ceramics, quartz, sapphire or plastics. For an electro-optical device (FIG. 1(a)), materials to make the transparent bottom substrate (5) include, but not limited to, quartz, glass, and sapphire. For electronic device (FIG. 1(b)) there is no special restriction on the optical property for the material used for the bottom substrate (20). Those of ordinary skill in the art will appreciate that if Si or other free standing electrode materials are used, the substrate (20) is not required.

The top surface of the device is also in contact with an electrode (2 & 17). A to electrode is included in the sensor to provide the second terminal to complete the electric circuit with the bottom electrode. While not limited in size, shape, material, or fabrication, the structure of the top layer (1,2 & 16,17) of the device including the electrode will depend on the stimuli (13 & 28) being sensed. For sensing distribution of stress or pressure on the area of contact by features including, but not limited to, texture, palpable structure, hardness inhomogeneity, the top electrode will typically be supported on a film of flexible material (1 & 16). This flexible substrate (1 & 16) that receives the stress or pressure stimuli is made of material including, but not limited to, plastics, metal foil, or other polymeric substances. The top electrode can either be in physical contact with the device or deposited on the device surface. In the former case, the electrode layer (2 & 17) will most likely be deposited on the flexible insulating substrate (1 & 16), respectively, prior to physical contact with the device; and in the latter case, the substrate (1 & 16) will most likely be deposited on the top electrode (2 & 17), respectively, after the deposition of the electrode on the multilayers (3 & 18), respectively.

Those of ordinary skill in the art will appreciate that the device will function without the top layer (substrate) (1 & 16) i.e. with a "bare" top electrode (2 & 17). The bare top electrode may be a flexible film made of conducting or semiconducting materials, including, but not limited to, a flexible metal or metal alloy sheet, a conducting polymer, a composite comprising of conducting and semi-conducting fillers in polymeric matrix. Typical examples known to experts include, but not limited to, Aluminum foil, Polyaniline film, silver or graphite particles filled polymer film, blends of conducting polymer with other polymers, and a metal film deposited on the device (3&18) by standard vapor deposition or sputtering processes. The to layer comprising substrates (1 & 16) on the top electrode (2 & 17) or simply the electrode with no substrate, is impervious to nanoparticles and in most cases will also serve as an encapsulation layer to protect the device.

For stimuli other than stress or pressure, depending on the ultimate use for the sensor, the substrates (1,5 & 16,20) and electrodes (2,4 & 17,19) at the bottom of the device (3 & 18) may be semi-flexible or rigid. To sense stimuli such as temperature, the backing of the top electrode (2 & 17) may be a rigid or a flexible insulating substrate (1 & 16) including, but not limited to, ceramic, glass, plastics, and quartz. Those of ordinary skill in the art will appreciate that no substrate (1 & 16) is required when the top electrode (2 & 17) may itself be a flexible, free-standing film made of conducting or semi-conducting materials, including, but not limited to, a flexible metal or metal alloy sheet, a conducting polymer, a conductive composite comprising of conducting or semi-conducting fillers in polymeric matrix.

To sense stimuli such as charge distribution on surfaces, the top electrode (2 & 17) will itself be a film made of poorly conducting, or ion-conducting, or semi-conducting materials. To measure stimuli from charge distribution on a dielectric surface, no top substrate (1 & 16) will be required. Examples for the top electrode to measure charge distribution include, but not limited to, semi-conducting elements and compounds, conducting polymers, poorly conductive composites comprising of conducting fillers in polymeric matrix. A poor conducting material in contrast to a conducting material is a substance that conducts charge but the resistivity is more than 1 $\Omega$-cm. An example of a poor conductor includes, but not limited to, a carbon filled rubber composite. Ion-conducting materials are solids or gels that allow transport of ions. Examples of ion-conducting materials include, but not limited to, polyelectrolyte films, such as polylysine, poly(styrene sulfonate), poly(amic acid). Examples of semi-conducting materials include, but not limited to, Si and conducting polymers, such as poly(aniline) and poly(thiophene).

To operate the device, a bias is applied between the electrodes (2,4 & 17,19). The bias is typically less than 100 V, preferably less than 30V, for example 20V. The bias produces a small current through the device that will depend upon the area of the device. On application of stress or pressure to the flexible top surface of the device, the device strain causes the particles to move closer by a small distance, for example less than 5 nm, such as 0.5 nm. The reversible strain causes a change in current (15 & 29) through the device for both the opto-electronic (FIG. 1(a)) and electronic (FIG. 1(b)) devices, respectively. The device current (15 & 29) increases monotonically as the magnitude of the local compressive strain increases. Additionally, for the electro-optical device (FIG. 1(a)), the device contains a layer of nanoparticles made from direct band-gap semiconductor (for example, 8), such as ZnS, CdS, and so on, there is a concomitant emission of electroluminescent light (14). The intensity of light, similar to the current, also increases monotonically as the magnitude of local compressive strain increases. The electroluminescent light is collected through the transparent bottom layers comprising of the transparent electrode (4) and the substrate (5).

Those of ordinary skill in the art will appreciate that there are numerous methods to receive the electronic signal (15 & 29) and feed it to signal processing modules and computer for data acquisition, computation, storage, and appropriate display. Similarly, the art will appreciate that the optical signal (14) can be received by a photo detector such as a digital camera, single photodiode, or photo diode array, and converted to an electronic signal that can be fed to signal processing modules and computer for data acquisition, computation, storage and appropriate display. One will further appreciate that the data acquisition and computation system can feed back to an electromechanical entity that holds the device and/or the power supply of the device to invoke a desired action. Examples of the desired action may be, but not limited to, change in applied contact pressure and modulation of the applied voltage, V (12 & 27).

To spatially resolve the distribution of the stimuli over the area of contact, that is a tactile device, the full configuration has to be considered. For example, the stimuli include, but not limited to, stress or pressure by pressing the device against a palpable body, surface temperature of a body, non-uniformly charged dielectric surface. Experts in the art will appreciate the configurations described in FIG. 2, are just typical examples of the electro-optical and electronic devices. To someone skilled in this art, several obvious modifications and extensions are possible including, but not limited to, different pattern of the electrodes (31,33 & 42,44) and lateral patterning of the multilayer structure rather than a continuous film (32 & 43).

In the two typical configurations for the opto-electronic (FIG. 2(a)) and electronic (FIGS. 2(b) & 2(c)) tactile device discussed below, the convention for top and bottom parts of the devices is the same as that in FIG. 1 described above.

Figure 2A:
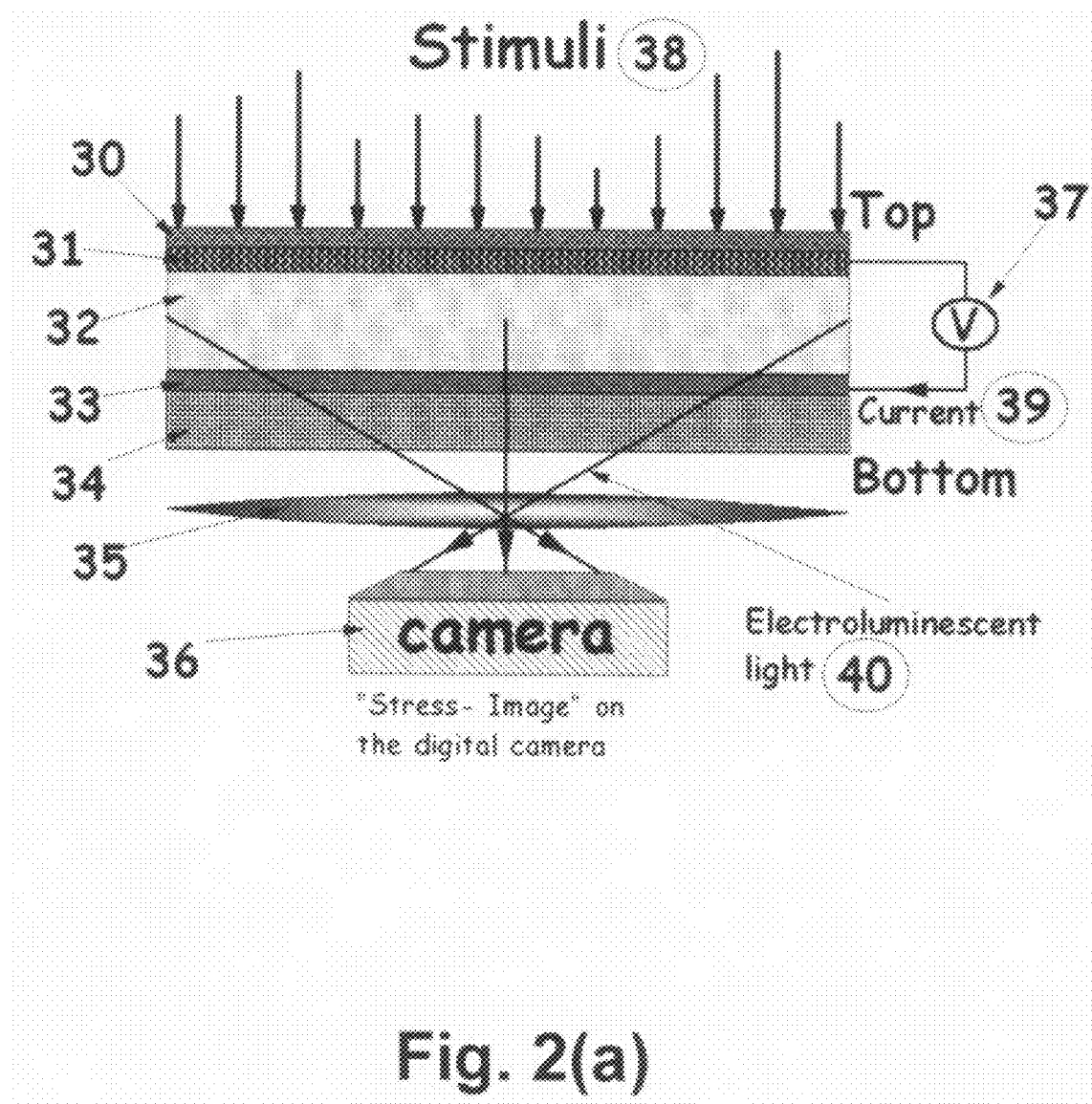
FIG. 2(a) is a cross-section of a typical configuration of an opto-electronic tactile device showing the digital camera as the optical detector.

Typical configuration to detect the distribution of the stress or pressure over the area of contact by an opto-electronic tactile device (FIG. 2(a)) is based on the device element (FIG. 1(a)) and requires a photo detector device (36) to focus (35) the electroluminescent light distribution (40) from the multilayer structure (32). The materials and thickness of top substrates (1 & 30), bottom substrates (5 & 34), top electrodes (2 & 31), bottom electrodes (4 & 33), and the layered structure of nanoparticles and dielectric (3 & 32) are identical for the opto-electronic device element (FIG. 1(a)) and the opto-electronic tactile device (FIG. 2(a)), respectively. Generally, the thickness of the multilayer structure will be well below 100 µm, preferably below 1 µm leading to no significant distortion of the distribution caused by difference in focusing due to finite thickness of the structure (32).

On application of stimuli (38), such as stress or pressure distribution over the area of contact on the top layer of the device which may be a flexible, insulating substrate (30) or a bare electrode (31) without the top substrate (30), the layers or nanoparticles in the multilayer (32) will come closer together. Similar to the opto-electronic device element (FIG. 1(a)), on biasing the device with voltage, V (37), both the intensity of electroluminescent light (40) and the current (39) will increase monotonically as the magnitude of the stress or pressure increases. As described earlier for the device element (FIG. 1(a)), because the top layer (30,31) or the bare to electrode (just 31) is flexible, the compressive strain in the multilayer (32) will correspond to the distribution of the applied strain or pressure such that the compressive strain will be larger where the magnitude of the stress or pressure is larger than the average stress or pressure over the whole contact area. Furthermore, similar to the device element (FIG. 1(a)), because the conductivity of the nanoparticle layer is limited to less than 1 µm, preferably less than 100 nm, the corresponding current in the higher strain region will be higher than the average strain over the area of contact. As a result, similar to the device element (FIG. 1(a)), the corresponding intensity of electroluminescence will be larger in the higher strain region than the average intensity over total area of contact. Thus, by focusing the electroluminescent light through the transparent bottom electrode (33) and transparent substrate (34) using focusing optics (35) on a photo detector (36), the distribution of strain and hence the stress or pressure is obtained.

The focusing optics (35) comprise optical components that include, but not limited to, lenses and microscope objectives. Examples of optical detectors (36) include, but not limited to, digital camera and array of photo diodes. Because the intensity of the light monotonically increases with increasing magnitude of the applied local stress or pressure, the stress-image obtained by the photo detector (36) will correspond to the distribution of the stimuli where the grey scale is proportional to the magnitude of the stimuli. Preferably, the magnitude of stress or pressure is linearly proportional to the intensity of electroluminescent light making the correspondence between the grey scale and stimuli distribution easy to interpret. The localized spatial distribution of current, and hence electroluminescence, is the resolution of the device (32), and is determined by the range of conduction in the lateral direction of the nanoparticle layers. Usually, the possible resolution of the multilayer device (32) which is less than 1 µm, preferably less than 100 nm, will be significantly smaller than the resolution of the optical detector (36). Thus, the resolution of the configuration will be determined by the optical detector (36) and the focusing optics (35). Details on the corresponding electronic signal (39) will be discussed in reference to the electronic tactile device (FIG. 2(b)), as it will require the top (31) and bottom (33) electrodes to be patterned. However, if the two electrodes are continuous films, the current (39) will be proportional to the average stress or pressure over the total area of contact.

To detect temperature and charge distribution, the materials and thickness of to substrates (1 & 30), bottom substrate (5 & 34), top electrode (2 & 31), bottom electrode (4 & 33), and the layered structure of nanoparticles and dielectric (3 & 32) are identical for the opto-electronic device element (FIG. 1(a)) and the opto-electronic tactile device (FIG. 2(a)), respectively. Those of ordinary skill in the art will appreciate that because the charge and temperature stimuli will be converted to an electronic signal by the optical detector (36), the operation, data acquisition, data processing/computation, data storage, and display, will be similar to the stress or pressure stimuli.

There are numerous methods to process the optical signal converted to an electronic signal by the photo detector (36) by feeding it to signal processing modules and computer for data acquisition, computation, storage, and appropriate display. Further the data acquisition and computation system can feed back signal to an electromechanical entity that holds the device and/or the power supply of the device to invoke a desired action. Examples of the desired action on feed back may be, but not limited to, change in applied contact pressure and modulation of the applied voltage, V (12 & 37). Those of ordinary skill in the art will appreciate that an interesting feedback criteria to the device would include, but not limited to, the current (39) that corresponds to the average stress or pressure over the contact area in case when the top (31) and bottom (33) electrodes are continuous and the peak electroluminescent intensity detected on the photo detector (36).

Figure 2B:
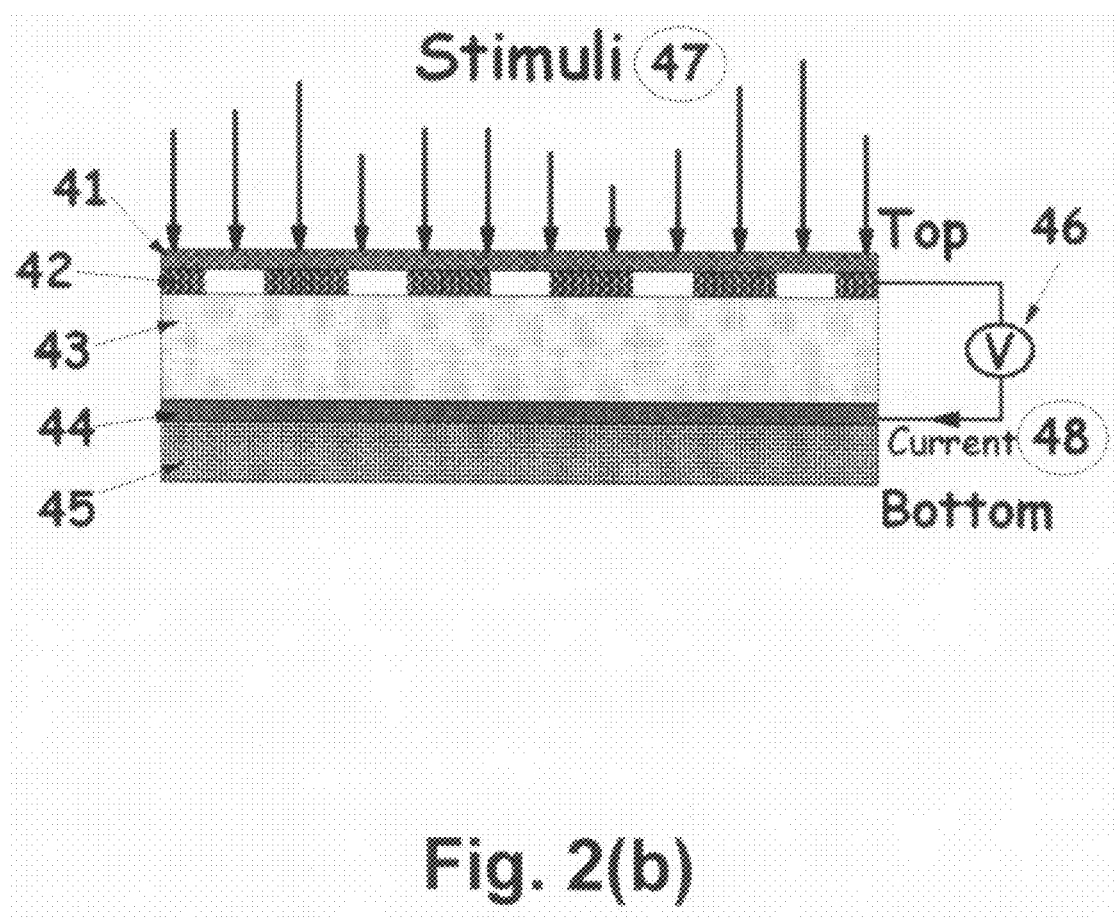
FIG. 2(b) is a cross-section of an Electronic tactile device.

Typical configuration to detect the distribution of the stress or pressure over the area of contact by an electronic tactile device (FIG. 2(b)) is similar to the electronic device element (FIG. 1(b)) with an additional feature to detect distribution of current (48) over the area of contact rather than just the total current (29) as discussed for the element. There are numerous electrode designs to measure the current distribution including, but not limited to, parallel set-of-lines of electrodes (42, 44 in FIGS. 2(c) and 2(b)). The materials and thickness of top substrates (16 & 41), bottom substrates (20 & 45), top electrodes (17 & 42), bottom electrodes (19 & 44), and the layered structure of nanoparticles and dielectric (18 & 43) are identical for the electronic device element (FIG. 1(b)) and the electronic tactile device (FIG. 2(b)), respectively.

On application of stimuli (47), such as stress or pressure distribution over the area of contact on the top layer of the device which may be a flexible, insulating substrate (41) or a bare electrode (42) without the top substrate (41), the layers of nanoparticles in the multilayer (43) will come closer together. Similar to the electronic device element (FIG. 1(b)), on biasing the device with voltage, V (46), the current (48) will increase monotonically as the magnitude of the stress or pressure increases. As described earlier for the device element (FIG. 1(b)), because the top layer comprising of substrate (41) and electrode (42) is flexible, the compressive strain in the multilayer (43) will correspond to the distribution of the applied strain or pressure such that the compressive strain will be larger where the magnitude of the stress or pressure is larger than the average stress or pressure over the whole contact area. Furthermore, similar to the device element (FIG. 1(b)), because the conductivity of the nanoparticle layer is limited to less than 1 µm, preferably less than 100 nm, the corresponding current in the higher strain region will be higher than the average strain over the area of contact.

Figure 2C:
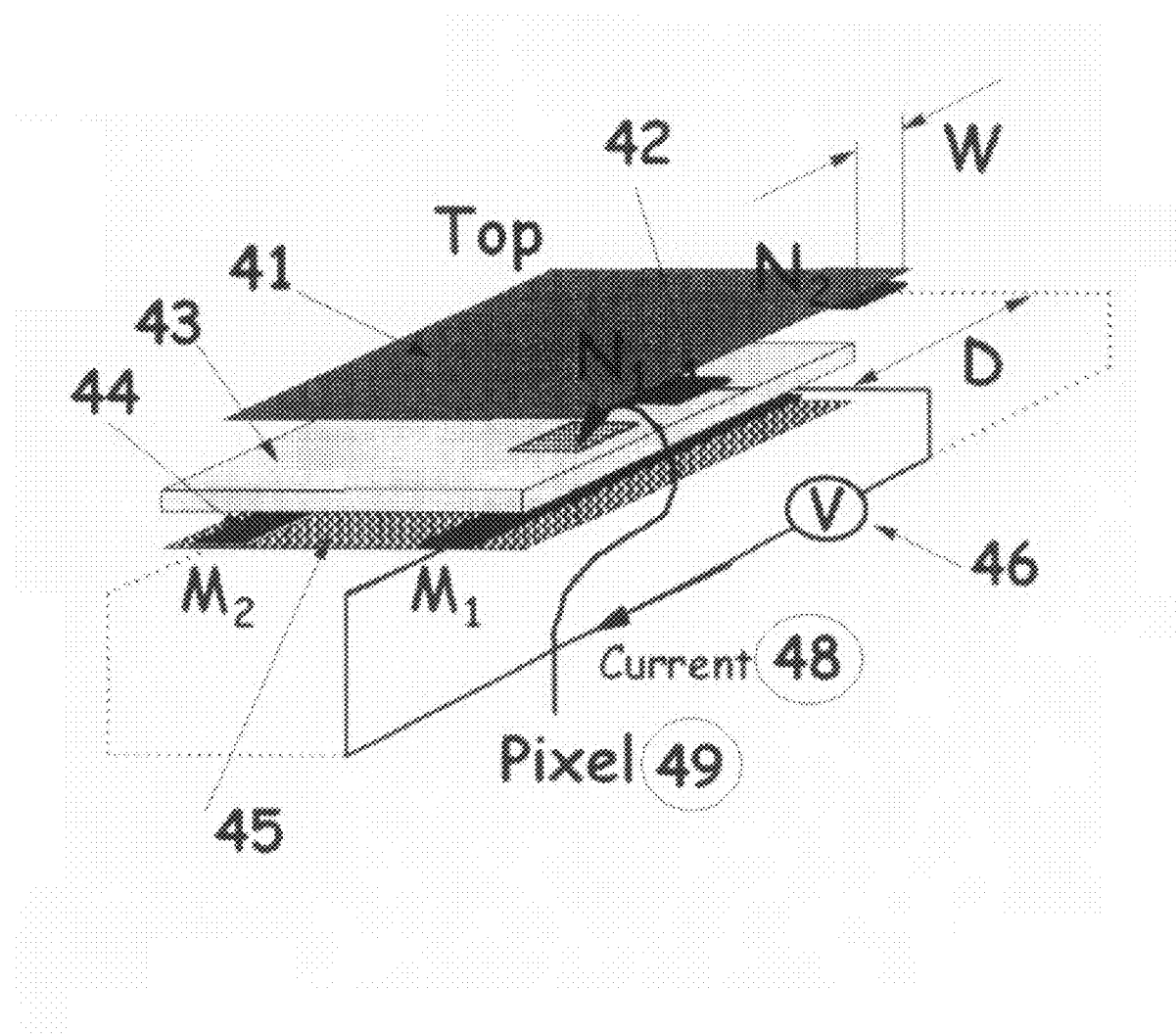
FIG. 2(c) is a typical pattern of the top and bottom electrodes to measure the current density over the area of contact to detect the stimuli.

The current distribution over the area of contact can be mapped by the particular device described in FIGS. 2(b) and 2(c), which is merely one example among many different possible combinations of electrode patterns. In the device described in FIGS. 2(b) and 2(c), the electrodes are parallel set-of-lines at the top (42) and bottom (44) of the multilayer device (43). Arbitrarily, to facilitate the description; the width and periodicity of the lines are W and D, respectively; and the number of lines in the top (42) and bottom (44) electrodes are N and M, respectively (FIG. 2(c)). Furthermore, the set-of-lines in the top and bottom electrode are mutually perpendicular forming an N by M array of pixels where the lines "sandwich" portion of the multilayer device (43). Those of ordinary skill in the art will appreciate that the set-of-lines in the top and bottom do not have to be of similar size. Typically, W and D are greater than 1 µm, preferably greater than 10 µm. Typically, N and M may range from 1 to 10,000. If a bias, V (46) is applied between lines $N_1$ and $M_1$ the current (48) will flow through the pixel (49) defined by the overlap region of the two lines (FIG. 2(c)). The current (49) will correspond to the strain localized to the pixel of cross-section W by W (49). It is well known to experts in the art that using standard electronics, the bias, V (46) can be spanned between all permutations of N lines at the top and M lines at the bottom to form an image with N times M pixels. For those of ordinary skill in the art will appreciate that there are numerous methods to process the N by M matrix of magnitude of current that correspond to the strain distribution resulting from the applied stress or pressure by feeding the current distribution (48) to signal processing modules and computer for data acquisition, computation, storage, and appropriate display. Those of ordinary skill in the art appreciate that the N by M matrix may be mapped to display the image of the stress or pressure distribution where the grey scale corresponds to the magnitude of current or proportional to the stimuli of local stress or pressure. Preferably, the magnitude of stress or pressure is linearly proportional to the local current measured on the pixel, making the correspondence between the grey scale and stimuli distribution easy to interpret. Those of ordinary skill in the art will further appreciate that the data acquisition and computation system can feed back signal to an electromechanical entity that holds the device and/or the power supply of the device to invoke a desired action. Examples of the desired action on feed back may be, but not limited to, change in applied contact pressure and modulation of the applied voltage, V (46).

The localized spatial distribution of current is the resolution of the multilayer device (43) and is determined by the range of conduction in the lateral direction of the nanoparticle layers in the multilayer device (43). Similar to the device element (FIG. 1(b)), because the lateral conductivity of the nanoparticle layer is limited to less than 1 µm, preferably less than 100 nm, the resolution of the multilayer device (43) is less than 1 µm, preferably less than 100 nm. Usually, the resolution of the electrode pattern which is the periodicity, D (FIG. 2(c)), is greater than 1 µm. Thus, the resolution of the electronic device configuration will be determined by D.

For those of ordinary skill in the art will appreciate that there are numerous methods to process the N by M matrix of current (48) from the parallel set-of-lines by feeding it to signal processing modules and computer for data acquisition, computation, storage, and appropriate display. Those of ordinary skill in the art will further appreciate that the data acquisition and computation system can feed back signal to an electromechanical entity that holds the device and/or the power supply of the device to invoke a desired action. Examples of the desired action on feed back may be, but not limited to, change in applied contact pressure and modulation of the applied voltage, V (27 & 46). Those of ordinary skill in the art will appreciate that an interesting feedback criteria to the device would include, but not limited to, the average current that corresponds to the average stress or pressure over the contact area that may be computed from the N by M matrix of current, and the peak current among the N by M matrix of current-magnitudes.

To detect temperature and charge distribution, materials and thickness of top substrates (16 & 41), bottom substrates (20 & 45), top electrodes (17 & 42), bottom electrodes (19 & 44), and the layered structure of nanoparticles and dielectric (18 & 43) are identical for the electronic device element (FIG. 1(b)) and the electronic tactile device (FIG. 2(b)), respectively. Because the charge and temperature stimuli will also be converted to an N by M matrix of magnitude of currents, the operation, data acquisition, data processing/computation, data storage, and display, will be similar to that for the stress or pressure stimuli.

For those of ordinary skill in the art will appreciate that a tactile device configuration to simultaneously detect the distribution of the stimuli by measuring both the electronic (i.e., device current) and optical (i.e., electroluminescent light) signals is possible by replacing the continuous thin film electrodes (31, 33) of the opto-electronic tactile device (FIG. 2(a)) with patterned electrodes (42,44). In such a device, the rest of the components and all the materials will be similar to the opto-electronic tactile device described above (FIG. 2(a)).

The above application emphasizes a device composed of nanoparticles to achieve distribution of the stimuli on physical contact at high spatial resolution. For example, in certain optimum designs the resolution to resolve texture will be comparable or better than a human finger sense. Furthermore, in certain optimum designs the optical and electronic signal will be linearly proportional to applied stress or pressure making the grey level of "stress-image" quantitatively comparable to the distribution of the stimuli. Designs composed of well established materials allow simple deposition processes that are possible, but not limited to, at room temperature under ordinary conditions that does not require exceptional environmental control, such as high quality clean room. A highly attractive advantage of the composition and design of the thin film tactile devices (FIG. 2) is that it can be made on surfaces of arbitrary curvature, for example, cylindrical surfaces to make fingers for humanoid robots to emulate human fingers. Furthermore, the device may be conformally placed on a surface of complex curvature that may be soft or hard, flexible or rigid, and flat or curved.

A general method to fabricate the multilayer device (3, 32 & 18,43) comprises sequential deposition of dielectric barrier layers ((7,9 & 22,24) and nanoparticle layers (6,8, 10 & 21,23,25) on unpatterned or patterned bottom electrode (4,33 & 19,44), supported on a substrate (4,34 & 20,45) by a well established process of dip coating known as electrostatic self-assembly. In dip coating, the bottom substrate with electrode is immersed in an aqueous solution of charged dielectric polymer called polyelectrolyte or suspension of charged nanoparticles. To ensure integrity of the layered structure (3,32 & 18, 43) the sequence of materials deposited will have opposite charges. For example, the process may commence with dip coating the bottom electrode surface with positively charged polyelectrolyte followed by dip coating of negatively charged polyelectrolyte. This process of alternate dip coating of the two electrolytes may continue for several cycles, preferably 2 to 10 cycles to form the dielectric barrier layer. The subsequent monolayer of nanoparticle is deposited by similar dip coating on the surface of the dielectric layer. If the charge on the nanoparticle is negative in the suspension, the charge of the last polyelectrolyte deposited in the dielectric barrier layer will be positive. The nanoparticle layer can also be thickened by dip coating an intermediate layer of polyelectrolyte of opposite charge to the nanoparticle. This principle can be repeated to deposit alternate layers of dielectric barrier and nanoparticles to form the multilayer device (3,32 & 18,43). The chemistry and structure of the nanoparticle layers may vary among the nanoparticle layers. Similarly, each of the dielectric layers may also have different physical and chemical structure depending on the polyelectrolytes used for dip coating. Finally the top electrode may be contacted as described above.

REFERENCES

The following references provide background information on the field relative to the present invention,.

1. Robles-De-La-Torre, G. & Hayward, V. Force can overcome object geometry in the perception of shape through active touch. *Nature* 412, 445-448 (2001).
2. Dario, P., Guglielmelli, E. & Laschi, C. Humanoids and personal robots: Design and experiments. *Journal of Robotic Systems* 18, 673-690 (2001).
3. Okumura, Y. et al. morph3: a compact-size humanoid robot system capable of acrobatic behavior. *Advanced Robotics* 18, 699-710 (2004).
4. Wurtz, R. P. Vision and touch for grasping. *Sensor Based Intelligent Robots* 2238, 74-86 (2002).
5. Matsumoto, S. et al. A tactile sensor for laparoscopic cholecystectomy. *Surgical Endoscopy-Ultrasound and Interventional Techniques* 11, 939-941(1997).
6. Wellman, P. S., Dalton, E. P., Krag, D., Kern, K. K., Howe, R. D. Tactile imaging of breast masses" First clinical report. Arch Surg, 136, 204-208 (2001).
7. Howe, R. D. Tactile Sensing and Control of Robotic Manipulation. *Advanced Robotics* 8, 245-261 (1994).
8. Jia, Y. B. Localization of curved parts through continual touch. *IEEE Transactions on Robotics* 21, 726-733 (2005).
9. Tajima, R., Kagami, S., Inaba, M. & Inoue, H. Development of soft and distributed tactile sensors and the application to a humanoid robot. *Advanced Robotics* 16, 381-397 (2002).
10. Okamura, A. M. & Cutkosky, M. R. Feature detection for haptic exploration with robotic fingers. *International Journal of Robotics Research* 20, 925-938 (2001).
11. Shikida, M., Shimitzu, T., Sato, K. & Itoigawa, K. Active tactile sensor for detecting contact force and hardness of an object. *Sensors and Actuators A-Physical* 103, 213-218 (2003).
12. Engel, J., Chen, J. & Liu, C. Development of polyimide flexible tactile sensor skin. *Journal of Micromechanics and Microengineering* 13, 359-366 (2003).
13. Howe, R. D. & Cutkosky, M. R. Dynamic Tactile Sensing—Perception of Fine Surface-Features with Stress Rate Sensing. *IEEE Transactions on Robotics and Automation* 9, 140-151 (1993).
14. De Rossi, D., Carpi, F. & Scilingo, E. P. Polymer based interfaces as bioinspired 'smart skins'. *Advances in Colloid and Interface Science* 116, 165-178 (2005).
15. Someya, T. et al. A large-area, flexible pressure sensor matrix with organic field-effect transistors for artificial skin applications. *Proceedings of the National Academy of Sciences of the United States of America* 101, 9966-9970 (2004).
16. Morley, J. W., Goodwin, A. W. & Darian-Smith, I. Tactile discrimination of gratings. *Experimental Brain Research* 49, 291-299 (1983).
17. Johansson, R. S. & LaMotte, R. H. Tactile detection thresholds for a single asperity on an otherwise smooth surface. *Somatosensory Research* 1, 21-31 (1983).
18. Decher, G. Fuzzy nanoassemblies: Toward layered polymeric multicomposites *Science* 277, 1232-1237 (1997).
19. Cassagneau, T., Mallouk, T. E. & Fendler, J. H. Layer-by-layer assembly of thin film zener diodes from conducting polymers and CdSe nanoparticles: *Journal of the American Chemical Society* 120, 7848-7859 (1998).

The invention claimed is:

1. An active sensor device, for converting external stimuli applied by physical contact with the sensor surface to a signal, comprising:
    a. a thin flexible film
    b. first and second electrodes, disposed on the top and bottom surfaces, respectively, of the thin flexible film for electrical contact with the thin film;
    c. at least one layer of nanoparticles in the thin film between the electrodes, said nanoparticles being placed under strain upon the physical contact with the sensor surface;
    d. at least one layer of a dielectric barrier layer on the either side of the at least one nanoparticle layer, said barrier layer having a thickness of less than 25 nanometers and conductivity less than $10^{-9} \Omega^{-1} \cdot cm^{-1}$;

e. at least one substrate to support the device that does not make physical contact with the stimuli; and f. means for applying an electrical current between said first and second electrodes, said electrical current flowing by tunneling through said dielectric barrier layers and said nanoparticles and being modulated by the strain placed on the nanoparticles upon the physical contact with the sensor surface to thereby provide a signal indicative of the physical contact.

2. A sensor in accordance with claim 1 wherein the nanoparticles comprise at least one of conducting and semi-conducting materials.

3. A sensor in accordance with claim 2 wherein the nanoparticles comprise at least one of: CdS, ZnS, CdSe, ZnSe, BN, IP, Au, Ag, Au coated $SiO_2$, Au coated TiO2, Au coated Co, and FePt coated $Fe_3O_4$.

4. A sensor in accordance with claim 1 wherein the dielectric barrier layer is selected from a group of polyelectrolytes, and insulating polymers, or combinations thereof.

5. A sensor in accordance with claim 4 wherein the dielectric barrier layer is selected from a group of: poly(styrene sulfonate), deoxyribo nucleic acid, poly(lysine), poly(allylamine hydrochloride), and polystyrene.

6. A sensor in accordance with claim 1 wherein the dielectric barrier layer and the nanoparticle layer alternate to form a multilayer stack.

7. A sensor in accordance with claim 1, wherein:
a) the second electrode and the substrate are transparent; and
b) at least one layer of nanoparticles in the multilayer stack are composed of electroluminescent nanoparticles, wherein upon applying a potential between the electrodes the stimuli applied by physical contact with the first electrode modulates the electroluminescent light from the multilayer stack and the current through the said stack.

8. A sensor in accordance with claim 7 wherein the modulated electroluminescent light from the multilayer stack is collected through the bottom of the device and focused on a photo-detector.

9. A sensor in accordance with claim 1 wherein the first electrode is selected from the group of: aluminum foil, poly(aniline) thin film, silver or graphite particle filled polymer film, blends of conducting polymer with polyelectrolytes, and metal thin films deposited on the stack surface.

10. A sensor in accordance with claim 1 wherein first electrode is covered with a flexible substrate selected from a group of: insulating materials comprising polyimides, polyamides, polyesters and elastomers.

11. A sensor in accordance with claim 1, wherein:
a) the first electrode is covered with a flexible substrate; and
b) the first and second electrodes are patterned to allow measurement of the modulation of local current through the stack.

12. A sensor in accordance with claim 11 wherein the pattern of the electrodes comprises parallel set of lines and wherein the lines for the top and bottom electrode are disposed at 90° with respect to each other.

13. A sensor in accordance with claim 11 wherein the said patterned first electrode is selected from a group of: poly(aniline) thin film, silver or graphite particle filled polymer film, blends of conducting polymer with polyelectrolytes, and metal thin film lines deposited on the stack surface or the top substrate.

14. A sensor in accordance with claim 11 wherein the said patterned second electrode is selected from a group of: transparent conducting, semi-conducting, or composite of conducting or semiconducting fillers in an insulating polymer matrix material including Indium-Tin oxide, and a carbon nanotube filled polymer composite.

15. A sensor in accordance with claim 11 further including means for measuring the modulated current distribution of the patterned electrode due to said stimuli and computer means to display the spatial distribution of current corresponding to the stimuli.

16. A sensor in accordance with claim 6, wherein:
a. the first electrode is covered with a flexible insulating substrate;
b. the second electrode is supported on an insulating substrate; and
c. the said first and second electrode are patterned to allow measurement of the modulation of local current through the stack.

17. A sensor in accordance with claim 1 wherein the nanoparticles in the at least one layer of nanoparticles have an average diameter of less than 100 nm and a polydispersity index of less than 10.

* * * * *